US006524235B2

United States Patent
Mitsumori

(10) Patent No.: US 6,524,235 B2
(45) Date of Patent: Feb. 25, 2003

(54) ENDOSCOPIC IMAGE PICKUP ASSEMBLY

(75) Inventor: Naotake Mitsumori, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/858,569

(22) Filed: May 17, 2001

(65) Prior Publication Data

US 2001/0044571 A1 Nov. 22, 2001

(30) Foreign Application Priority Data

May 22, 2000  (JP) ........................................ 2000-149272

(51) Int. Cl.[7] ................................................ A61B 1/06
(52) U.S. Cl. ........................................ 600/167; 358/98
(58) Field of Search ................................ 600/167, 182, 600/112, 108, 325; 358/98, 55

(56) References Cited

U.S. PATENT DOCUMENTS

| | | | | |
|---|---|---|---|---|
| 4,784,144 A | * | 11/1988 | Ono et al. | 600/325 |
| 4,807,026 A | * | 2/1989 | Nishioka et al. | 358/98 |
| 4,868,646 A | * | 9/1989 | Tsuji | 358/98 |
| 4,882,619 A | * | 11/1989 | Hasegawa et al. | 358/55 |
| 4,926,257 A | * | 5/1990 | Miyazaki | 358/98 |
| 5,235,965 A | * | 8/1993 | Hiroya | 600/108 |
| 5,609,561 A | * | 3/1997 | Uehara et al. | 600/112 |
| 5,895,350 A | * | 4/1999 | Hori | 600/167 |
| 6,251,068 B1 | * | 6/2001 | Akiba et al. | 600/182 |
| 6,409,658 B1 | * | 6/2002 | Mitsumori | 600/167 |

OTHER PUBLICATIONS

U.S. patent application Ser. No. 09/671,168, filed Sep. 28, allowed.
U.S. patent application Ser. No. 09/858,569, filed May 17, pending.
U.S. patent application Ser. No. 10/134,544, filed Apr. 30, pending.

* cited by examiner

Primary Examiner—Teresa Walberg
Assistant Examiner—Leonid M Fastovsky
(74) Attorney, Agent, or Firm—Oblon, Spivak, McClelland, Maier & Neustadt, P.C.

(57) ABSTRACT

A fixed lens of an optical objective lens system is fixedly retained on a support member which is provided in a rigid tip end section of an endoscopic insertion instrument, along with a movable lens or lenses which are movable toward and away from the fixed lens in the direction of optical axis of the objective lens system. A drive means for the movable lenses is coupled with the support member, while an image sensor means is located at the focus of the objective lens system. A guide means which guides the support member of an optical assembly in the direction of the optical axis is connected to the image sensor means. The support member is slid along the guide means to adjust the optical objective lens system into an in-focus position with respect to the image sensor means. After adjusting the position of the optical objective lens system, the support member is fixed to the guide means by the use of an optical assembly fixation means.

7 Claims, 9 Drawing Sheets

ENDOSCOPIC IMAGE PICKUP ASSEMBLY

BACKGROUND OF THE INVENTION

1. Field of the Art

This invention relates to an endoscope for use in medical examinations, and more particularly to an endoscopic image pickup assembly with an objective lens drive mechanism to move by remote control a plural number of lens groups of an optical objective lens system, to be incorporated into an observation window on a rigid tip end section at the distal of an elongated insertion instrument of an endoscope, for example, for the purpose of adjustmenting at least focal depth, image magnification rate or view field angle.

2. Prior Art

Generally, endoscopes which are in use for medical purposes are largely constituted by a manipulating head assembly to be gripped and manually operated by a hand of an operator, an elongated insertion instrument extended on the front side of the manipulating head assembly for insertion into a body cavity of a patient, and a universal cable which is led out from the manipulating head assembly and disconnectibly connected to a light source. For its functions, the elongated insertion instrument of an endoscope is successively constituted by, from its fore distal end, a rigid tip end section, an angle section and a flexible body portion. The flexible body portion occupies the major length of the elongated insertion instrument from a proximal end portion which is connected to the manipulating head assembly, and arranged to be bendable in arbitrary directions along a path of insertion. The rigid tip end section contains an illumination window or windows, an image pickup means, and an opening of a biopsy channel through which forceps or other instrument is introduced into a body cavity. The angle section is can be angularly bent by remote control from the manipulating head assembly, for turning the rigid tip end section into an arbitrary direction.

As mentioned above, the rigid tip end section contains at least an illumination window and an image pickup means. Located within the illumination window is a light emitting end of a light guide which is constituted by a bundle of fiber optics. The light guide is extended as far as the above-mentioned universal cable via the manipulating head assembly and disconnectibly connected to a light source. On the other hand, as the image pickup means, an optical objective lens system is fitted in an observation window on the rigid tip end section. In the case of an electronic endoscope, a solid-state image sensor device is located at the focus of the optical objective lens system. In the case of an optical endoscope, an image pickup end of a light guide, which is constituted by a bundle of fiber optics, is located at the focus of the optical objective lens system. A signal cable which is connected from the solid-state image sensor device or the image guide is passed through the insertion instrument along with the light guide and extended to the manipulating head assembly. An electronic endoscope which appears in the following description can be read and taken as an optical endoscope if a solid-state image sensor device and a signal cable is replaced by an image guide.

In addition to the above-mentioned component parts, an exit opening of a biopsy channel is provided on the rigid tip end section. Connected to the exit opening is a biopsy channel which is constituted by a flexible tube. Further, a wash nozzle is provided on the rigid tip end section to wash clean the observation window when contaminated. An air/water feed tube is connected to the wash nozzle. These biopsy channel and air/water feed tube are extended as far as the manipulating head assembly through the elongated insertion instrument of the endoscope.

As described above, an elongated insertion instrument of an endoscope is normally required to accommodate bundles of fiber optics, signal cable, biopsy channel and a number of feed tubes. In order to bend the angle section as described above, a pair of upper and lower operating wires or two pairs of vertical and horizontal operating wires are also passed through the insertion instrument. The fore ends of these operating wires are fixed either to the rigid tip end section or to a structural member in the proximity of the rigid tip end section. Within the angle section, the positions of the operating wires are restricted in circumferential direction. Further, the respective operating wires are extended as far as the manipulating head assembly through the flexible section of the endoscopic insertion instrument.

The optical objective lens system of the image pickup, which is normally constituted by a plural number of lenses, should preferably be capable of adjustments in focal depth, image magnification and view field angle, depending upon the position of an intracavitary portion to be examined or upon the purpose of examination. In this regard, it has been known to make part of the lenses of the optical objective lens system movable in the direction of optical axis for adjustments of focal depth, image magnification or view field angle.

As for drive means for moving a movable lens in the direction of optical axis of the objective lens system, it has been the general practice to use a control cable for shifting the position of a movable lens or lenses by remote control. In such a case, the fore end of a control cables is connected to the movable lens, while the proximal end of the cable is extended into the manipulating head assembly in such a way that an operator can shift the position of a movable lens in the direction of optical axis by remote control from the head assembly. More particularly, a control cable of this sort is usually composed of a flexible sleeve and a number of transmission members which are fitted in the flexible tube.

In this regard, in order to add to the optical objective lens system a function of varying a magnification rate, for example, it is the general practice to move, in the direction of optical axis, a movable lens assembly consisting of one or a plural number of lens groups. In the case of an optical objective lens system which permits higher image magnifications, however, difficulties are encountered in strictly positioning respective lens components and failures in this regard invariably result in unclear unfocused images. Therefore, it becomes necessary to make adjustments to remove not only machining errors which might have occurred in the machining stages of lens frames, support members and other components of an image pickup device, but also assembling errors which might have occurred in an assembling stage of the image pickup assembly. For this purpose, after assembling together an optical objective lens system and an image sensor means of an endoscopic observation unit, fine adjustments of lens positions are usually required with regard to at least part of lens components which are employed in the endoscopic observation unit.

An endoscopic observation unit including an image pickup assembly requires fine adjustments of lens positions of an optical objective lens system in a stage subsequent to its assembling stage as disclosed, for example, in Japanese Laid-Open Patent Application H11-47074. In the case of this endoscopic observation unit, a cover lens which is designed to function as a first lens of the objective lens system is located at a fore distal end of an insertion instrument, and a movable lens tube which carries a plural number of movable lenses is located behind the cover lens and movably supported on an objective lens frame. The objective lens frame is pulled back and forth to vary the distance between the movable lenses and a solid-state image sensor device. In order to adjust the focus on the image sensor after assembling the optical system into the endoscopic observation unit, the movable lens tube is moved in the direction of the optical axis toward or away from the objective lens frame. For this purpose, a lens adjustment hole is bored through the objective lens frame, and the lens tube is moved by an adjustor rod which is inserted into the adjustment hole. Further, upon completion of adjustment into an in-focus position, the lens tube is fixedly clamped to the objective lens frame by tightening set screws against the objective lens frame.

In this connection, as generally known in the art, the observation unit to be fitted into an insertion instrument of an endoscope is extremely small in size, particularly in diameter and thickness of the optical objective lens system, with movable lenses fitted in a lens tube which is extremely short in length in the direction of the optical axis. Accordingly, it suffices for the movable lens tube, which is mounted on an objective lens frame or other support member, to be moved over an extremely small distance in the direction of the optical axis. This means that fine adjustment of the distance between the movable lens tube and an image sensor device is very difficult and requires meticulous skills. In addition, due to a difficulty of securing a sufficient length of fitting engagement of the movable lens tube with the support member, misalignment or deviation of the optical axis is very likely to occur when the lens tube is fastened to an adjusted position by the use of setting screws. Further, in a case where a movable lense tube is arranged to slide on and along a lens frame, there is still another problem that abraded particles or dust occurring in sliding portions of the lens tube can deposit on lens surfaces.

SUMMARY OF THE INVENTION

In view of the difficulties as mentioned above, it is an object of the present invention to provide an endoscopic image pickup assembly which is arranged to facilitate fine adjustments of the position an optical objective lens system after assembling same into the image pickup assembly and which can fix the optical objective lens system precisely in a correct position after fine adjustments.

In accordance with the present invention, for achieving the above-stated objective, there is provided an endoscopic image pickup to be incorporated into a rigid tip end section of an endoscopic insertion instrument, the image pickup comprising: a support member; an optical assembly mounted on the support member, and composed of an objective lens system having at least a fixed lens and a movable lens adapted to move toward and away from the fixed lens in the direction of optical axis and a drive means for the movable lens; an image sensor means having a solid-state image sensor device to be located at the focus of the objective lens system; a guide means connected to the image sensor means to guide the support member of the optical assembly in the direction of optical axis of the objective lens system; and an optical assembly fixation means for fixing the support member to the guide means after sliding the support member along the guide means to bring the objective lens system into an in-focus position with respect to the image sensor device.

The optical objective lens system includes at least a fixed lens and a movable lens, each consisting of one or a plural number of lens elements. The movable lens can be constituted either by one movable lens group (consisting of one or a plural number of lens elements) or by two movable lens groups which are movable independently of each other. In the case of an objective lens system with two movable lens groups, the drive means can be constituted by a cam member which is connected to lens frames of the two movable lens groups, and a rotational drive member which is coupled with the cam member. The support member is constituted by a housing which permits movements of the two lens groups. A fixed lens frame is fixedly retained on the housing, which is provided with an optical system holder portion adapted to guide sliding movements of the movable lens frames along the inner periphery of the housing, along with a cam mount portion adapted to encase the cam member. In one particular form, the above-mentioned guide means is constituted, for example, by a slide guide which is provided with an arcuate guide surface for slidably accommodating the optical system holder portion of the housing, and an outlet opening for passing at least part of the cam mount portion of the housing to the outside. An entrance opening is provided at one end of the slide guide for installation of the optical system holder portion. The optical assembly fixation means may be set screws or an adhesive which is filled in gap spaces between the outlet opening of the slide guide and the housing to fix the optical assembly in position. In case the image sensor means is provided with a prism for turning a light path from the optical objective lens system through 90 degrees, one end of the slide guide, the end away from the above-mentioned outlet opening, can be fixedly bonded to the prism by the use of an adhesive or the like.

The above and other objects, features and advantages of the present invention will become apparent from the following particular description of the invention, taken in conjunction with the accompanying drawings which show by way of example some preferred embodiments of the invention.

PREFERRED EMBODIMENTS OF THE INVENTION

Figure 1:
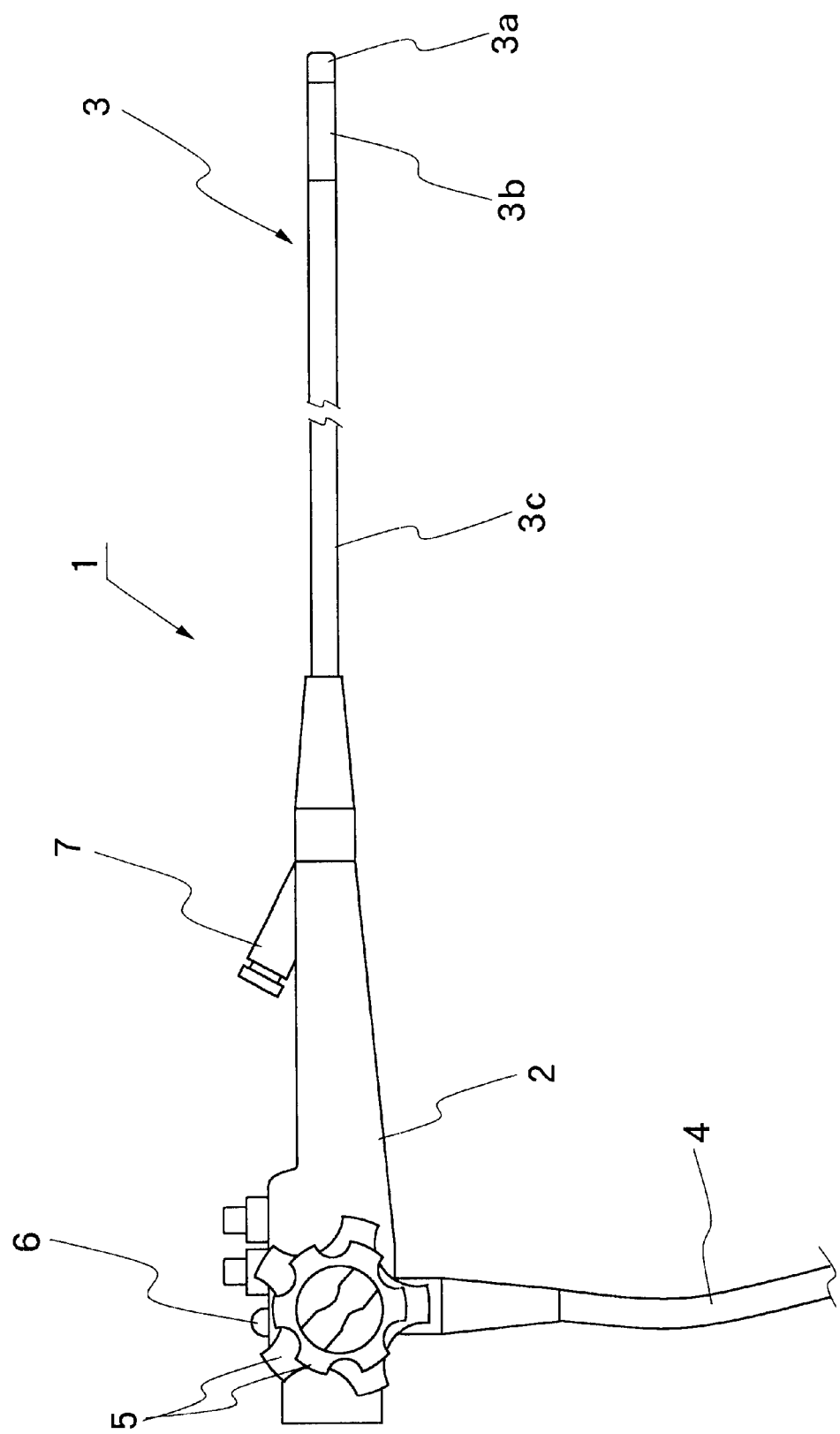
FIG. 1 is a schematic view of an endoscope embodying the present invention.
Figure 2:
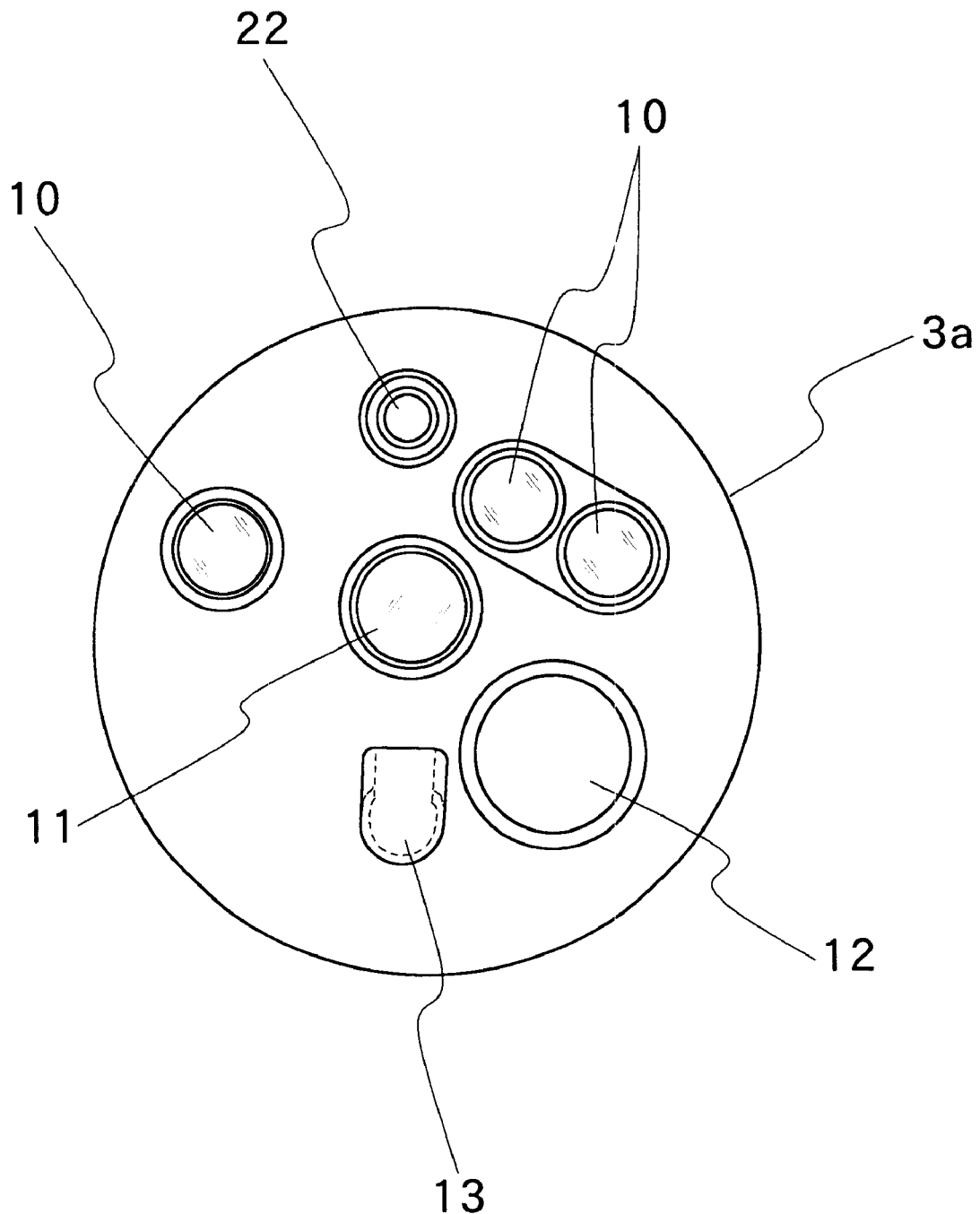
FIG. 2 is an outer view of a distal end face of an insertion instrument of the endoscope.

Referring first to FIG. 1, there is schematically shown the general layout of an endoscope. As seen in this figure, the endoscope 1 is largely constituted by a manipulating head assembly 2, an elongated insertion instrument 3 which is extended out on the front side of the manipulating head assembly 2 for insertion into a patient's body cavity or the like, and a universal cable which is led out on the rear side of the manipulating head assembly 2. For the functions required, the insertion instrument 3 is composed of, from its fore distal end, a rigid tip end section 3a, an angle section 3b and a flexible body section 3c.

The rigid tip end section 3a is housed in a casing of a rigid material and provided with illumination windows 10, an observation window 11, an outlet opening 12 of a biopsy channel, a washer nozzle 13 and so forth. In this instance, as shown in the drawing, the illumination windows 10 are normally provided at a plural number of positions on the opposite sides of the observation window 11. By manipulating an angle knob 5 which is provided on the manipulating head assembly 2, the angle section 3b can be bend in upward, downward, rightward and leftward directions to turn the rigid tip end section 3a into a desired direction. Further, the flexible body section 3c, which occupies a major portion of the entire length of the insertion instrument 3, is arranged to have a structure which has flexibility in bending directions along with resistance to crushing, so that it can be bent in arbitrary directions in a path of insertion which may contain turns and bends.

Figure 3:
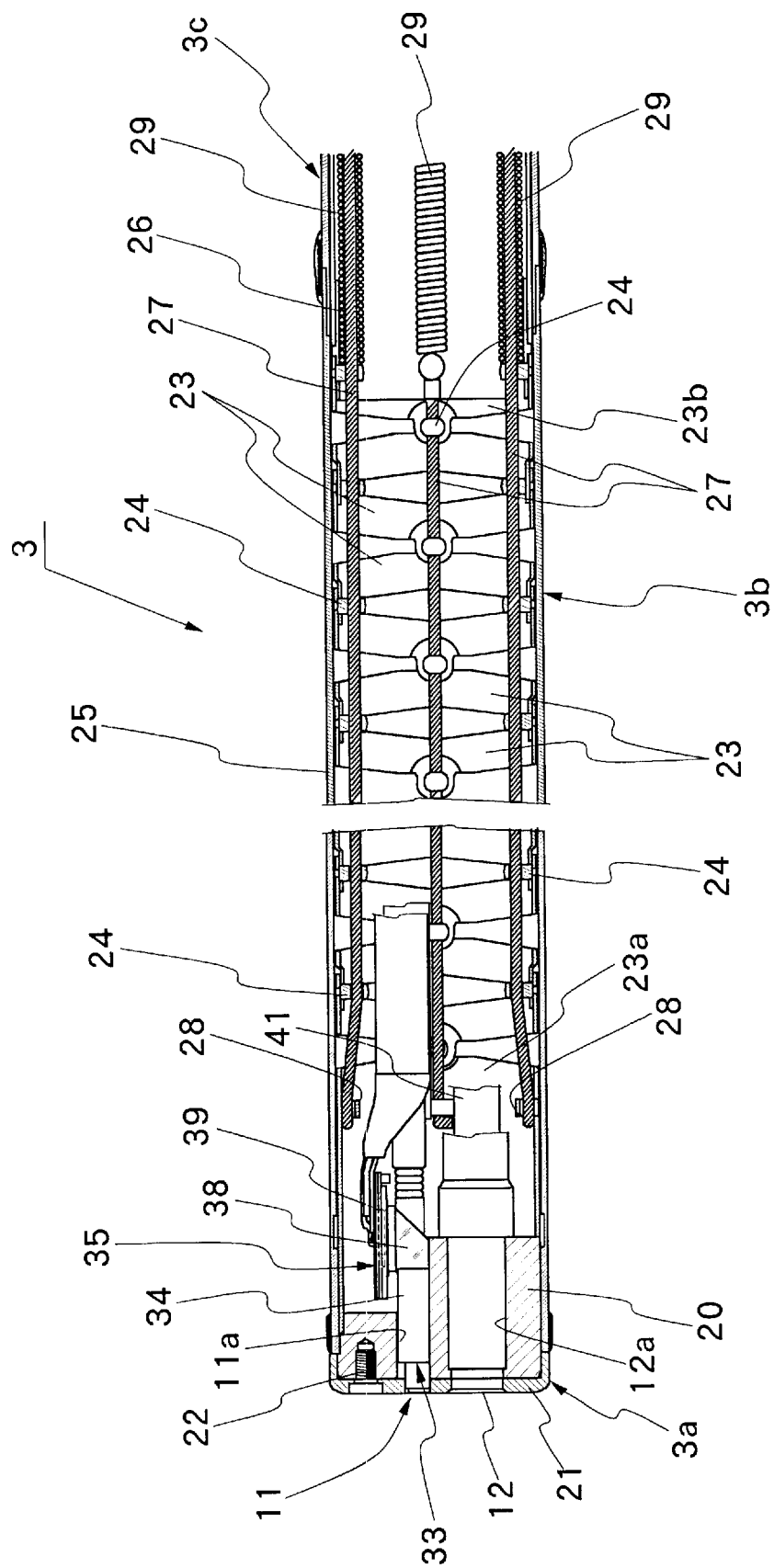
FIG. 3 is a schematic longitudinal section taken through the distal end face of the endoscopic insertion instrument.

Shown in FIG. 3 is a cross section across a fore end portion of the insertion instrument 3. As seen in that figure, the rigid tip end section 3a is provided with a casing block 20 with a number of axial through holes or bores. Fitted on the fore end face of the casing block 20 is cap 21 which is securely fixed to the casing block 20 by means of stop screws 22. The angle section 3b is constituted by a series of angle rings 23 which are successively and connected one after another into the fashion of pivotally connected flexible nodal rings by the use of pivot pins 24. Fitted around the nodal ring structure of angle section 3b is a cover member 25, which is normally constituted by an inner layer of metal wire mesh and an outer skin layer of EPDM or the like. The foremost one of the angle rings 23, that is, an angle ring 23a in the foremost position is fixedly fitted on the core block 20 of the rigid tip end section 3a. On the other hand, the angle ring 23b on the side of the proximal end of the angle section 3a, that is, the angle ring 23b in the rearmost position is fixedly secured by welding or soldering to a connector ring 26 which connects the angle section 3a with the flexible body portion 3c. The flexible body section 3c is constituted by a metal coil tube, metal wire mesh which is fitted around the metal coil tube, and an outer skin layer formed further around the metal wire mesh. The construction of the flexible body portion 3c is omitted in the drawings since it is well known in the art.

Figure 4:
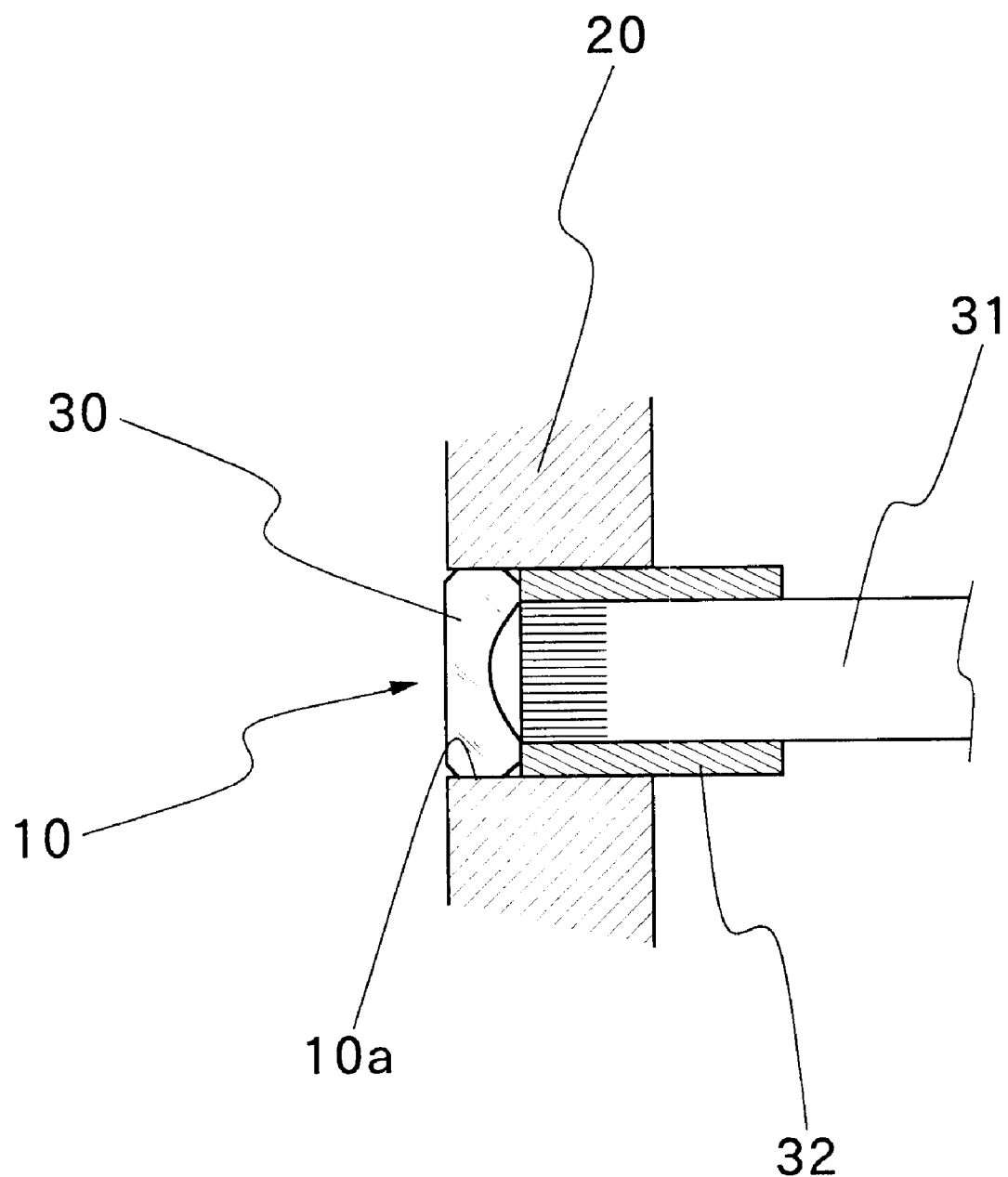
FIG. 4 is a schematic view of an illuminating section of the endoscopic insertion instrument.

As shown in FIG. 4, the illumination windows 10 are each constituted by an opening 10a which is bored through the casing block 20, an illumination lens 30 which is fitted in the opening 10a, and a light guide 31. Illumination light which is emitted from the fore end of the light guide 31 is dispersed through the illumination lens 30 to irradiate broad areas. The light guide 31 is constituted by a bundle of a multitude of fine fiber optics. Except a fore end portion which is fitted in an frame ring 32 of the window opening 10a, the light guide 31 is loosely bundled in a freely flexible state by the use of a flexible tube or the like, and extended into the universal cable 4 through the insertion instrument 3 and via the manipulating head assembly 2.

Figure 5:
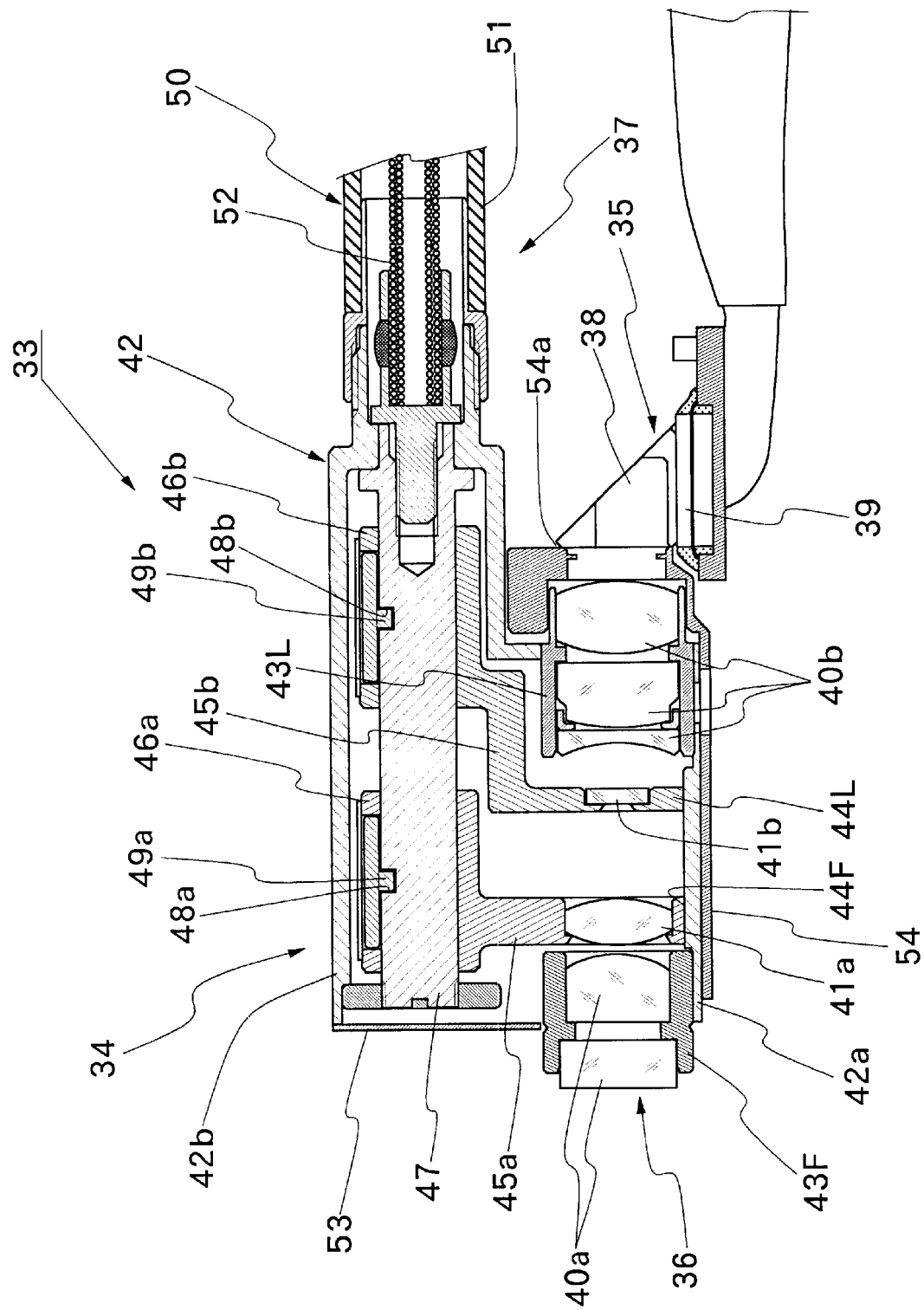
FIG. 5 is a schematic longitudinal section of an image pickup assembly.
Figure 6:
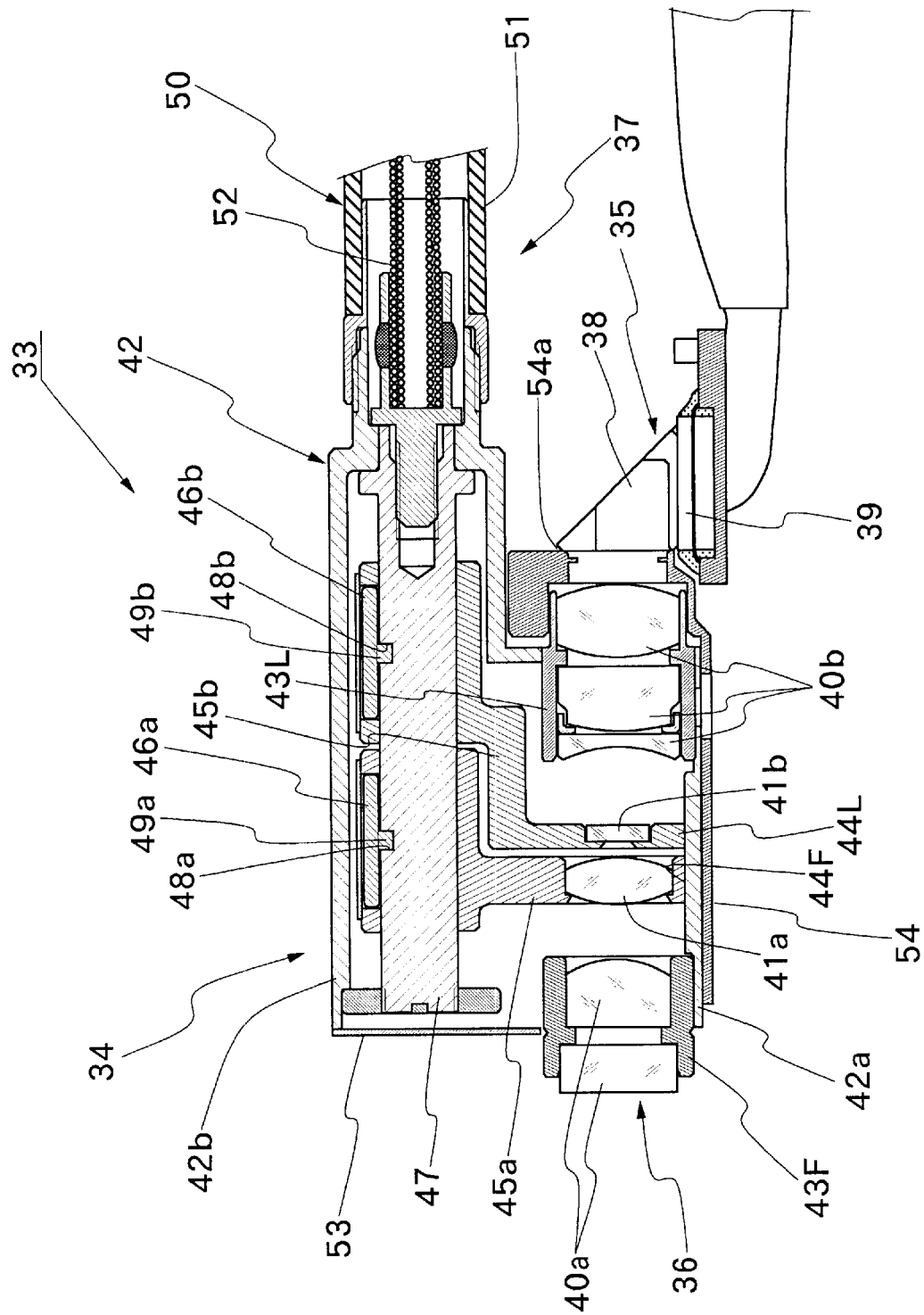
FIG. 6 is a view similar to FIG. 5 but showing the image pickup assembly in a different operational phase.

Fitted in position behind the observation window 11 at the fore distal end of the endoscopic insertion instrument is an image pickup assembly 33. As seen in FIGS. 5 and 6, the image pickup assembly 33 is supported in a cylindrical cavity 20a which is bored into the casing block 20 in the axial direction of the insertion instrument 3. The image pickup assembly 33 is composed of an optical subassembly 34 and an image sensor subassembly 35. The optical subassembly 34 is constituted by an optical objective lens system 36 and its drive means 37. The image sensor subassembly 35 includes a prism 39 for turning light path of the optical objective lens system 36 through 90 degrees, and a solid-state image sensor element 40 which is located at the focus of the optical objective lens system 36.

The optical object lens system 36 is constituted by a fixed lens groups 40a and 40b each consisting of a single or a group of a plural number of lens elements, and movable lens groups 41a and 41b each consisting of a single or a plural number of lens elements, which are movable in the direction of optical axis of the objective lens system 36 and encased in a housing 42. In this instance, the movable lenses groups 41a and 41b are located between the fixed lenses groups 40a and 40b and are moved toward and away from each other to provide, for example, a zooming action.

The fixed lens groups 40a and 40b are respectively mounted on fixed lens frames 43F and 43L. Provided between the fixed lens frames 43F and 43L are movable lens frames 44F and 44L for the two movable lens groups 41a and 41b, respectively. The movable lens frames 44F and 44L are moved in the direction of the optical axis through a cam member. Arms 45a and 45b are connected to the movable lens frames 44F and 44L, respectively. Fore distal ends of the arms 45a and 45b are terminated with ring members 46a and 46b, respectively. Regarding the optical objective lens system, it is to be understood that the present invention is not limited to the particular arrangements shown. For example, it can be arranged to have only one fixed lens group and one to three movable lens groups, if desired.

At a position distant from the optical objective lens system 36, a cam shaft 47 is located in parallel relation with the optical axis of the optical objective lens system 36. The cam shaft 47 is provided with two cam grooves 48a and 48b on its circumferential surface. On the other hand, cam pins 49a and 49b are provided on the ring members 46a and 46b for engagement with the cam grooves 48a and 48b, respectively. As the cam shaft 47 is turned in a forward or reverse direction, the cam pins 49a and 49b are slid in a forward or rearward direction in and along the cam grooves 48a and 48b, respectively, causing the movable lens groups 41a and 41b on the movable frames 44F and 44L to displace forward or rearward in the direction of the optical axis of the objective lens system through the ring members 46a and 46b and the arms 45a and 45b.

A control cable 50 is provided as a rotational drive means for the cam shaft 47. In the particular embodiment shown, the control cable 50 has a flexible shaft 62 of tightly would coils passed as flexible rotation transmission members through a flexible sleeve 51 which is connecting to the housing 8. The fore end of the flexible shaft 52 is connected to the cam shaft 47, while its rear end is connected to a rotational drive means such as an electric motor or the like. As the rear end of the flexible shaft 52 is rotated about its longitudinal axis by the rotational drive means, the rotation is transmitted to the cam shaft 47. As the cam shaft 47 is put in rotation, the movable lens frames 44F and 44L are moved toward or away from each other in the direction of the optical axis.

Figure 7:
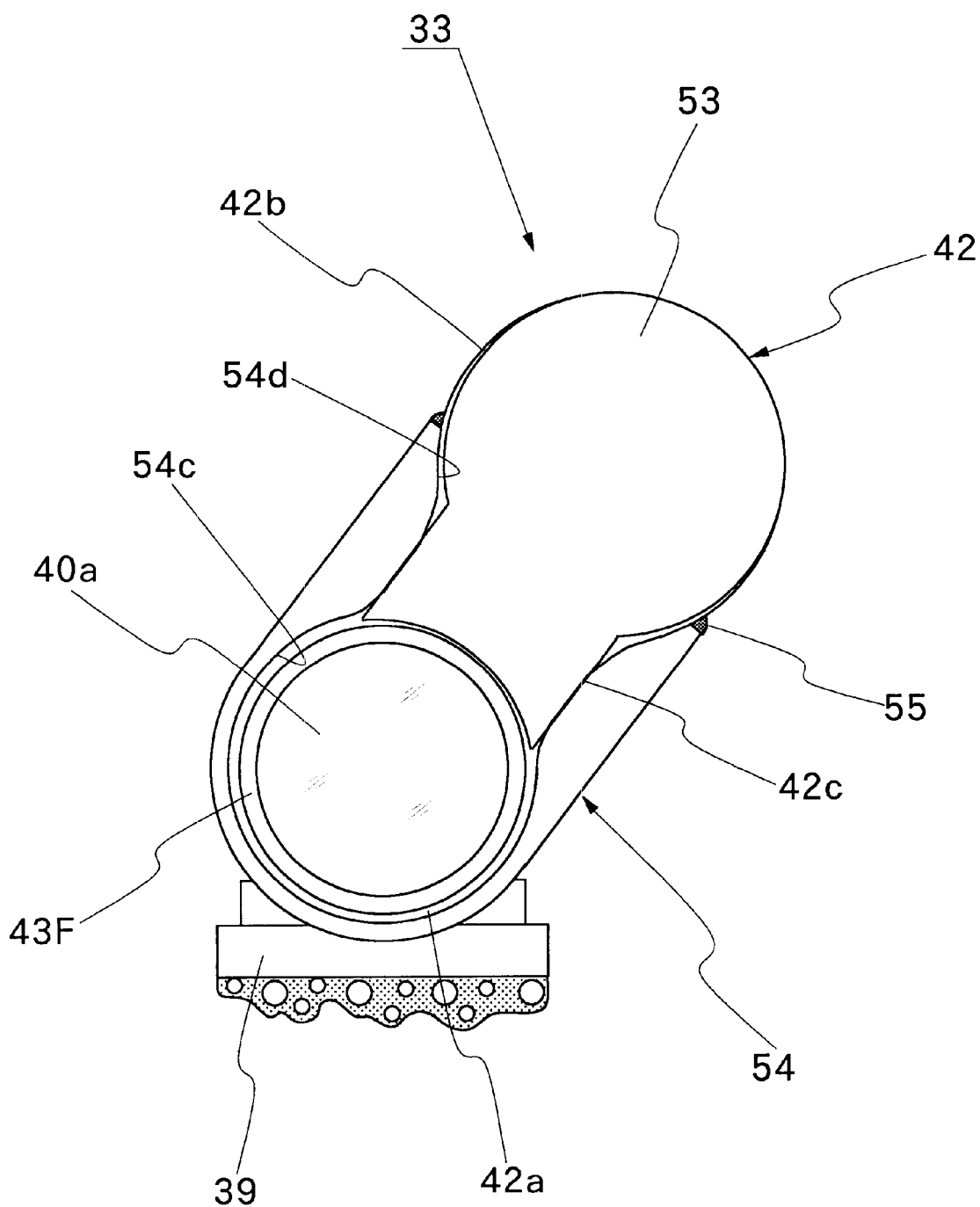
FIG. 7 is a left-hand side view of the image pickup assembly of FIG. 5.

As seen in FIG. 7, the housing 42 is provided as a support member for the optical subassembly 34, and formed with an optical system holder portion 42a and a cam mount portion 42b on its lower and upper sides, respectively. The optical system holder portion 42a and the cam mount portion 42b are both constituted by a circular member and connected with each other by a bridge portion 42 which is narrow in width. The fixed lens frames 43F and 43L are fixedly retained in the optical system holder portion 42a, which is provided with a guide surface for guiding axial movements of the movable lens frames 44F and 44L. On the other hand, the cam shaft 47 is fitted in the cam mount portion 42b, and arms 45a and 45b of the movable lens frames 44F and 44L are located internally of the bridge portion 42c.

The housing 42 is open at its fore end, through which the fixed lens frame 43b with the fixed lens group 40b, the cam shaft 47 and the movable lens frames 44F and 44L with the movable lens groups 41a and 41b and the fixed lens frame 43F with the fixed lens group 40a are successively assembled into the housing 42. Substantially a fore half portion of the fixed lens frame 43F is projected out of the housing 42, and its lens element in a foremost position serves also as cover glass. Further, after assembling these component parts, the fore end of the housing 42 is closed with an end cover 53 to hold its interiors substantially in a shielded state. A rear extension of the cam mount portion 42b is projected on the rear side of the housing 42, and the fore distal end of the flexible sleeve 51 of the control cable 50 is securely fixed to the rear extension of the cam mount portion 42b.

Figure 8:
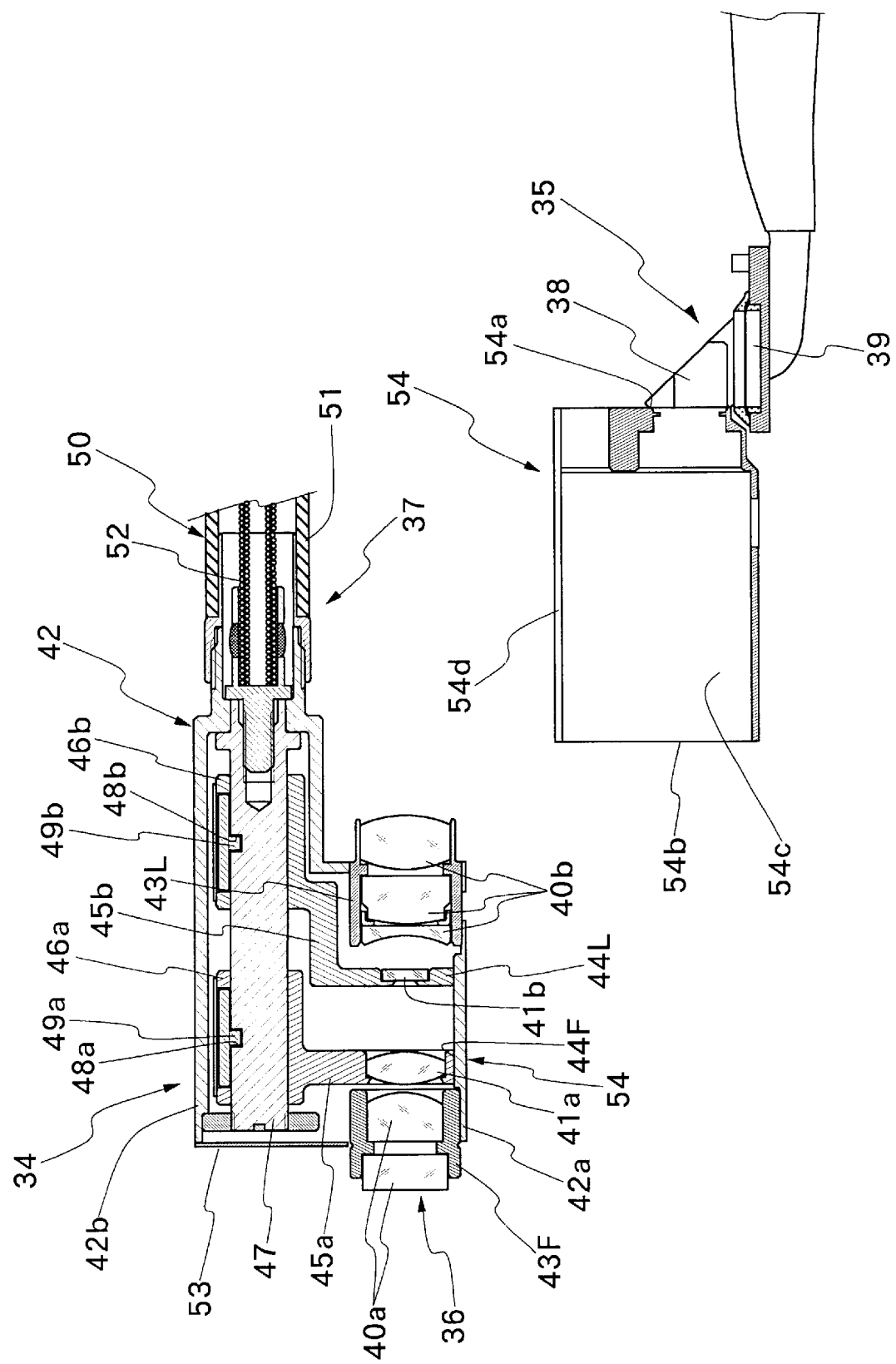
FIG. 8 is a view similar to FIG. 5 but showing an optical system assembly in a disassembled state.
Figure 9:
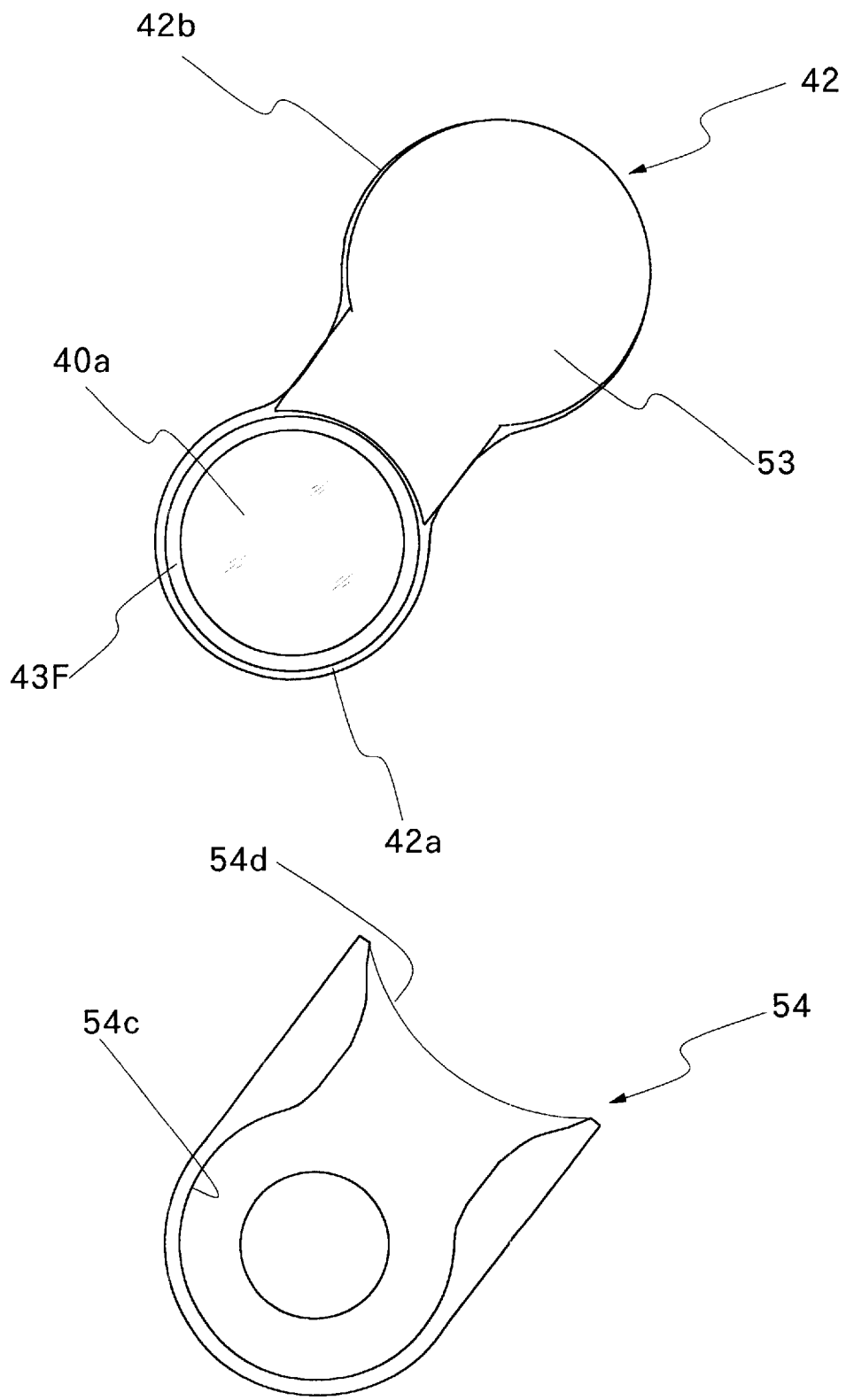
FIG. 9 is a left-hand side view of the optical system assembly shown in FIG. 8.

Further, as shown in FIGS. 8 and 9, a slide guide 54 is fixed to the prism 38, and the housing 42 of the optical objective lens system 34 and the drive means 37 is mounted on the slide guide 54. This slide guide 54 is constituted by a member which is formed substantially in U-shape and in a predetermined length, and provided with a joint surface 54a at one end which is securely fixed to a surface of the prism 38 by the use of an adhesive or other fixation means. Provided on the opposite end face of the slide guide 54 away from the joint surface 54a (i.e., the end face which is located on the front side when mounted on the rigid tip end section 3a) is an entrance opening 54b for receiving the optical subassembly 34. Provided on the interior side of the slide 54, contiguously from the entrance opening 54b, is an arcuate guide surface 54c which slidably guides thereon the optical system holder portion 42a of the housing 42. Further, provided at and along the upper end of the slide guide 54 is a passage opening 54d which is extended over the entire axial length of the slide guide 54. The upper passage opening 54d of the slide guide 54 is formed in a width which permits passage therethrough of the bridge portion 42c of the housing 42.

The optical subassembly 34, having all the lens groups of the optical objective lens system 36 mounted thereon, is assembled separately from the image sensor means 35. Then, the joint surface 54a of the slide guide 54 is fixed to a surface of the prism 38 of the image sensor means 35 by the use of an adhesive, followed by insertion of the optical system holder portion 42a of the housing 42 of the optical subassembly 34 into the slide guide 43 through the entrance opening 54b and along the inner guide surface 54c until the optical subassembly 34 is located in a predetermined position within the slide guide 54.

In this regard, the optical objective lens system 36 has to be adjusted and located in such a position that images on the image sensor device 39 are exactly in focus. For this purpose, the housing 42 is moved along the guide surface 54c of the slide guide 54. In so doing, the position of the objective lens system 36 should be adjusted in a very strict manner. The position of the housing 42 can be shifted in the direction of optical axis either by holding in one hand the cam mount portion 42b of the housing 42, which sticks out through the outlet opening 54d of the slide guide 54 or by engaging a suitable jig with the cam mount portion 42b. This adjustment of the position of the objective lens system 36 is complete as soon as it is located exactly in an in-focus position with respect to the image sensor device. Then, as a fixation means, an adhesive 55 is filled in the gaps between the outlet opening 54b of the slide guide 54 and the bridge portion 42c of the housing 42.

Mounted within the housing 42 are all of the lenses of the optical objective lens system 36, including the front and rear fixed lens groups 40a and 40b and the movable lens groups 41a and 41b which are positioned between the fixed lens groups 40a and 40b, along with the movable lens drive means 37 including the cam member which drives the movable lens groups 41a and 41b. Accordingly, the image pickup assembly as a whole present itself as a relatively large block. More specifically, since the optical system holder portion 42a is relatively lengthy in the direction of the optical axis, it can be held in fitting engagement with the slide guide 54 over an increased length. It follow that the image pickup assembly can be set easily in an adjusted position without experiencing misalignment or deviation errors of the optical system holder portion 42a, that is to say, without experiencing misalignment or deviation errors of the optical axis of the objective lens system 36.

Besides, the image pickup assembly, which is in the form of a relatively large block, can be easily handled in adjusting the optical objective lens system 36 strictly into an in-focus position as described above. Further, the cam member of the drive means 37 as well as the control cable 50 which rotationally drives the cam ember is connected to the housing 42, so that, once the objective lens system 36 is adjusted to an in-focus position, there is no need for adjusting the position of the drive means 37 afterwards. Furthermore, the position of the objective lens system 36 is adjusted by sliding, along the slide guide 54, the housing 42 which is substantially in a closed state. Therefore, the respective lens elements of the objective lens system are suitably protected against deposition of foreign matter or abraded particles which might occur as a result of sliding contact between the housing 42 and the slide guide 54.

Moreover, in adjusting the focusing position, the entire lens groups of the objective lens system are shifted together. Therefore, the above-described arrangements require a smaller margin of adjustment for the objective lens system as compared with a case where part of the lenses is moved for adjustment of the focus. Namely, it becomes possible to reduce the distance of displacement of the housing 42 in the slide guide 54 in bringing the objective lens system into an in-focus position. Consequently, it becomes possible to reduce the axial length of the image pickup assembly 33 as a whole and to reduce the total axial length of the rigid tip end section 3a of the endoscopic insertion instrument.

What is claimed is:

1. An endoscopic image pickup to be incorporated into a rigid tip end section of an endoscopic insertion instrument, said image pickup comprising:
   a support member;
   an optical assembly mounted on said support member, and composed of an objective lens system having at least a fixed lens and a movable lens adapted to move toward and away from said fixed lens in the direction of optical axis and a drive means for said movable lens;

an image sensor means having a solid-state image sensor device to be located at the focus of said objective lens system;

a guide means connected to said image sensor means to guide said support member of said optical assembly in the direction of optical axis of said objective lens system; and an optical assembly fixation means for fixing said support member to said guide means after sliding said support member along said guide means to bring said objective lens system into an in-focus position with respect to said image sensor device.

2. An endoscopic image pickup as defined in claim 1, wherein said movable lens is comprised of two movable lens groups adapted to move in the direction of said optical axis independently of each other, and said drive means comprises a cam shaft coupled with respective lens frames of said two movable lens groups and a rotational drive means coupled with said cam shaft.

3. An endoscopic image pickup as defined in claim 2, wherein said support member is constituted by a housing adapted to hold a lens frame of said fixed lens fixedly in position, and provided with an optical system holder portion adapted to guide sliding movement of said movable lens frames along inner peripheral surfaces thereof and a cam mount portion encasing said cam shaft therein.

4. An endoscopic image pickup as defined in claim 3, wherein said guide means is constituted by a slide guide provided with an arcuate guide surface for slidably accommodating said optical system holder portion of said housing, said slide guide being formed with an outlet opening to let at least part of said cam mount portion of said housing protrude to the outside therethrough and provided with an entrance opening at one end thereof for receiving said optical system holder portion.

5. An endoscopic image pickup as defined in claim 4, wherein said optical assembly fixation means is an adhesive filled in gap spaces between said outlet opening of said slide guide and said housing.

6. An endoscopic image pickup as defined in claim 4, wherein said image sensor means comprises a prism for turning a light path from said objective lens system through 90 degrees, and said slide guide is securely fixed to said prism at an end away from said entrance opening.

7. An endoscopic image pickup as defined in claim 3, wherein said movable lens drive means is constituted by a control cable having a flexible sleeve connected to said cam mount portion of said housing, and a flexible rotation transmission shaft fitted in said flexible sleeve and connected to said cam shaft.

* * * * *